United States Patent
Müller et al.

(10) Patent No.: US 10,571,391 B2
(45) Date of Patent: Feb. 25, 2020

(54) METHOD FOR ADJUSTING A MEASURING DEVICE

(71) Applicant: Endress+Hauser Conducta GmbH+Co. KG, Gerlingen (DE)

(72) Inventors: Frank Müller, Stuttgart (DE); Peter Lindmüller, Essingen (DE); Daniel Iten, Wernabwil (CH)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 31 days.

(21) Appl. No.: 15/819,643

(22) Filed: Nov. 21, 2017

(65) Prior Publication Data

US 2018/0156719 A1 Jun. 7, 2018

(30) Foreign Application Priority Data

Dec. 6, 2016 (DE) ........................ 10 2016 123 583

(51) Int. Cl.
*G01N 21/27* (2006.01)
*G01N 21/59* (2006.01)

(52) U.S. Cl.
CPC ......... *G01N 21/278* (2013.01); *G01N 21/274* (2013.01); *G01N 21/59* (2013.01); *G01N 2201/127* (2013.01)

(58) Field of Classification Search
CPC .... G01N 21/274; G01N 21/278; G01N 21/59; G01N 2201/127
USPC .................................................. 356/432–444
See application file for complete search history.

(56) References Cited

U.S. PATENT DOCUMENTS

| | | | | |
|---|---|---|---|---|
| 3,703,336 A | * | 11/1972 | Rosse | G01N 35/00594 356/39 |
| 3,960,497 A | * | 6/1976 | Acord | G01N 35/00693 422/67 |
| 4,482,251 A | | 11/1984 | Saylor | |
| 8,949,059 B2 | * | 2/2015 | Misener | G01N 21/274 702/104 |
| 8,993,956 B2 | * | 3/2015 | Engelhardt | G07D 7/12 250/252.1 |
| 2003/0107738 A1 | * | 6/2003 | Curtis | G01F 23/292 356/436 |
| 2006/0086196 A1 | * | 4/2006 | Rieder | G01F 1/8409 73/861.356 |
| 2009/0213380 A1 | | 8/2009 | Appel et al. | |
| 2010/0312483 A1 | * | 12/2010 | Peyser | G01N 33/52 702/19 |
| 2011/0061439 A1 | | 3/2011 | Dong et al. | |
| 2016/0231246 A1 | * | 8/2016 | Chu | C12Q 1/686 |

OTHER PUBLICATIONS

Search Report for German Patent Application No. 10 2016 123 583.0, German Patent Office, dated Jul. 27, 2017, 7 pp.

* cited by examiner

*Primary Examiner* — Isiaka O Akanbi
(74) *Attorney, Agent, or Firm* — Mark A. Logan; PatServe

(57) ABSTRACT

The present application relates to a method for adjusting a measuring device for measuring a measurand of a medium using at least one measuring sensor, including: laboratory calibration of the measuring device in a calibration solution, laboratory calibration of the measuring device in air, determination of a correction factor for correcting the laboratory calibration value of the measuring device in air to the laboratory calibration value of the measuring device in the calibration solution, on-site calibration of the measuring device in air, using the correction factor to correct the on-site calibration value of the measuring device in air, and on-site adjustment of the measuring device using the corrected on-site calibration value.

2 Claims, No Drawings

METHOD FOR ADJUSTING A MEASURING DEVICE

CROSS-REFERENCE TO RELATED APPLICATION

The present application is related to and claims the priority benefit of German Patent Application No. 10 2016 123 583.0, filed on Dec. 6, 2016, the entire contents of which are incorporated herein by reference.

TECHNICAL FIELD

The present application relates to a method for adjusting a measuring device for measuring a measurand of a medium using at least one measuring sensor.

BACKGROUND

Optical absorption measurements require a laboratory calibration value for determining physical variables such as extinction and the consequent transmission, absorption, etc. This laboratory calibration value is generally determined in a liquid calibration solution preferably, demineralized or ultrapure water.

Adjusting the laboratory calibration value to compensate for any system changes in the sensor over its lifespan is essential for achieving correct measurements. For this, a liquid calibration solution must be provided.

The quality of the laboratory calibration strongly depends upon the quality of the calibration solution. It cannot always be guaranteed that superior quality demineralized or ultrapure water is available on-site. These therefore need to be brought by the customer or service employee. Entrained materials from contaminated containers are possible. Moreover, to achieve satisfactory results, the measuring system and calibration solution must be in a thermodynamic equilibrium. Depending upon the application and differences in temperature between the two systems, this can take several minutes.

SUMMARY

The aim of the present application is to present a method for adjusting a measuring device that can be carried out over a short period.

The aim of the present application is achieved by the subject matter of the present application. The subject of the present application is a method for adjusting a measuring device for measuring a measurand of a medium using at least one measuring sensor, wherein the method includes:

laboratory calibration of the measuring device based upon at least one measurement signal detected by the measuring sensor in a calibration solution, laboratory calibration of the measuring device based upon at least one measurement signal detected by the measuring sensor in air, determination of a correction factor for correcting the laboratory calibration value of the measuring device, based upon at least one measurement signal detected by the measuring sensor in air, to a laboratory calibration value of the measuring device based upon at least one measurement signal detected by the measuring sensor in the at least one calibration solution, on-site calibration of the measuring device on the basis of at least one measurement signal detected by the measuring sensor in air, using the correction factor, correction of the on-site calibration value of the measuring device on the basis of at least one measurement signal detected by the measuring sensor in air, adjustment in particular, on-site adjustment of the measuring device using the corrected on-site calibration value.

DETAILED DESCRIPTION

Calibration in measuring technology is a measuring process for the reliable, reproducible determination and documentation of the deviation of a measuring device from another device which is, in this case, designated as normal. "Adjustment" is understood to be the most precise adjustment possible of the measuring device by a professional procedure.

To circumvent the unsteadiness of the calibration solution, for measuring sensors, the laboratory calibration value is adjusted to air using an optical absorption measuring method. The adjustment can be performed in water and air by using a correction factor that correlates the laboratory calibration value in water with the associated laboratory calibration value in air. The system-dependent correction function is initially determined in the laboratory calibration and saved in the sensor.

This method reduces the susceptibility to error with contaminated calibration solutions, since the quality of air is approximately constant. Moreover, the required time for adjustment is greatly reduced, since the difference in temperature between air and the measuring device to be adjusted is generally less than the difference in temperature between the measuring device to be adjusted and the calibration solution.

According to one advantageous variant, the at least one calibration solution is water in particular, ultrapure or demineralized water.

According to one advantageous development, the measuring sensor measures the measurand of the medium using optical absorption methods.

The method for adjusting the measuring device includes the following method steps. Initially, a laboratory calibration of the measuring device is performed. This includes the following method steps. First, the measuring sensor in the laboratory is immersed in water as the calibration solution, and a measurement signal of the measuring sensor is detected. The laboratory calibration value is determined in water using the detected measurement signal. Then, the laboratory calibration value of the measurement sensor is determined in air. A correction factor can be derived from the laboratory calibration value in water and the laboratory calibration value of the measurement sensor in air, by which the laboratory calibration value in air can be corrected to the laboratory calibration value in water.

The laboratory calibration is followed by the on-site calibration at the location where the measuring sensor is used, such as in a processing plant, which comprises the following steps. Initially, a measurement signal of the measuring sensor is detected in air, and the measuring sensor is calibrated on-site based upon the detected measurement signal, which yields an on-site calibration value. Subsequently, the on-site calibration value is, using the correction factor, corrected to the laboratory calibration value of a measuring sensor in water. Using the corrected on-site calibration value, the measuring sensor is adjusted (on-site).

A specific calculation example for determining the correction factor is presented below. A photodetector that serves as a measuring sensor provides a measurement signal of 10 a.u. (arbitrary unit for indicating the light intensity on the photodetector), and 8 a.u. in air. Accordingly, the laboratory calibration value of the measuring device in water is 10 a.u., and the laboratory calibration value of the measuring device in air is 8 a.u. This is initially determined in the laboratory prior to factory assembly. This yields a correction factor of 10 a.u./8 a.u.=1.25.

The invention claimed is:

1. A method for adjusting a measuring device for measuring a measurand of a medium using a measuring sensor, comprising:
    performing a first laboratory calibration of the measuring device based upon a first measurement signal detected by the measuring sensor in ultrapure or demineralized water, wherein the first laboratory calibration produces a first calibration value in water;
    performing a second laboratory calibration of the measuring device based upon a second measurement signal detected by the measuring sensor in air, wherein the second laboratory calibration produces a second calibration value in air;
    determining a correction factor for correcting the second calibration value in air to the first calibration value in water;
    performing an on-site calibration of the measuring device based upon a third measurement signal detected by the measuring sensor in air to produce an on-site calibration value in air;
    correcting the on-site calibration value in air to the first calibration value in water using the correction factor; and
    performing an on-site adjustment of the measuring device using the corrected on-site calibration value.

2. The method according to claim 1, wherein the measuring sensor is embodied to measure the measurand of the medium using optical absorption methods.

* * * * *